(12) United States Patent
Oogami (10) Patent No.: US 7,953,206 B2
(45) Date of Patent: May 31, 2011

(54) RADIOGRAPHIC IMAGE DETECTION APPARATUS

(75) Inventor: Satoru Oogami, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 81 days.

(21) Appl. No.: 12/585,687

(22) Filed: Sep. 22, 2009

(65) Prior Publication Data

US 2010/0074412 A1 Mar. 25, 2010

(30) Foreign Application Priority Data

Sep. 24, 2008 (JP) ................................ 2008-244057

(51) Int. Cl.
*H05G 1/64* (2006.01)
(52) U.S. Cl. .................................................. 378/98.12
(58) Field of Classification Search ............... 378/98.12
See application file for complete search history.

(56) References Cited

U.S. PATENT DOCUMENTS

| | | | | |
|---|---|---|---|---|
| 6,696,691 B2 * | 2/2004 | Wang et al. | ................... | 378/174 |
| 7,522,701 B2 * | 4/2009 | Jensen et al. | ................ | 378/98.12 |
| 7,742,569 B2 * | 6/2010 | Graumann | ................. | 378/98.12 |
| 2006/0072699 A1 * | 4/2006 | Mackie et al. | .................... | 378/4 |

FOREIGN PATENT DOCUMENTS

JP 2001-307085 11/2001

* cited by examiner

*Primary Examiner* — Chih-Cheng G Kao
(74) *Attorney, Agent, or Firm* — Jean C. Edwards, Esq.; Akerman Senterfitt

(57) ABSTRACT

In a radiographic image detection apparatus that can perform long-size radiography on a region of a patient that is larger than the detection range of a radiographic image detector, inclination of a radiographic image is corrected at high speed. The inclination angle of the radiographic image detector at each position Z within the movement range of the radiographic image detector is stored in a yawing table. When the inclination of the radiographic image is corrected, the inclination angle of the radiographic image detector is extracted from the yawing table based on the position at which each of the radiographic images is obtained, and the inclination angle of the radiographic image is corrected.

4 Claims, 5 Drawing Sheets

RADIOGRAPHIC IMAGE DETECTION APPARATUS

CROSS-REFERENCE TO RELATED APPLICATIONS

The present application claims priority from Japanese Patent Application No. 2008-244057, filed Sep. 24, 2008, the contents of which are herein incorporated by reference in their entirety.

BACKGROUND OF THE INVENTION

1. Field of the Invention

The present invention relates to a radiographic image detection apparatus that can perform so-called long-size radiography on a region that is larger than a detection range of a radiographic image detector.

2. Description of the Related Art

Conventionally, in medical fields and the like, long-size radiography (longitudinal radiography) is performed in some cases. In the long-size radiography, a radiographic image detector is moved with respect to a subject (patient) to obtain radiographic images at a plurality of positions, and the obtained radiographic images are combined. Therefore, in the long-size radiography, it is necessary that the radiographic image detector can move for a long distance (range) (for example, 180 cm). However, if an accurate stage that does not shift nor rotate even if the radiographic image detector moves for such a long distance is adopted, the cost of the apparatus becomes very high. Therefore, the mechanism of moving the radiographic image detector is provided by an aluminum extrusion rail that also functions as a support pole, and a bearing in many cases. In such cases, a gap (interval, space or the like) is provided between the rail and the bearing so that the movement mechanism operates smoothly even if the aluminum extrusion rail is warped, bent or the like.

Especially, when long-size radiography is performed to obtain an image of the entire vertebral column (spinal column, backbone), a length or an angle between joints is measured. Therefore, highly accurate synthesis of the image is required, compared with ordinary radiography. Especially, a rotation error (inclination) with respect to an axis perpendicular to a detection surface (plane) of the radiographic image detector causes shifting of image-overlapping areas. Therefore, even higher accuracy is required for the rotation error, compared with other kinds of errors.

Therefore, a method for synthesizing an image based on markers provided in a radiographic image detector has been proposed so that a plurality of radiographic images can be combined even if a mechanical shift in position, as described above, occurs (please refer to Japanese Unexamined Patent Publication No. 2001-307085 (Patent Literature 1), for example). In Patent Literature 1, markers that block radiation are provided at four corners of the radiographic image detector, and a radiographic image is obtained in such a manner that an image of the marker is included in the radiographic image. Further, rotation of a subject in a plurality of radiographic images is corrected based on images of the marker in the plurality of radiographic images.

However, when the inclination is detected by using the marker as disclosed in Patent Literature 1, it is necessary to perform image recognition processing, such as detecting the marker in the radiographic images. Therefore, there is a problem that a longer time is required to correct the inclination.

SUMMARY OF THE INVENTION

In view of the foregoing circumstances, it is an object of the present invention to provide a radiographic image detection apparatus that can correct inclination of a radiographic image at high speed.

A radiographic image detection apparatus of the present invention is a radiographic image detection apparatus comprising:

a radiation source that outputs radiation to a subject;

a radiographic image detector that detects, as a radiographic image, the radiation that has been output from the radiation source and transmitted through the subject;

a detector movement means that moves the radiographic image detector parallel to a radiation detection surface of the radiographic image detector;

a yawing table that stores an inclination angle of the radiographic image detector at each position of the radiographic image detector within a movement range of the radiographic image detector by the detector movement means;

an image correction means that corrects, based on the position of the radiographic image detector when each of a plurality of radiographic images is obtained by the radiographic image detector moved to different positions from each other, inclination of the plurality of radiographic images respectively by using the yawing table; and an image synthesis means that produces a synthesis image by combining the plurality of radiographic images corrected by the image correction means.

Here, the type of the radiographic image detector is not limited as long as the radiographic image detector detects radiation that has passed through the subject as a radiographic image. For example, the radiographic image detector may be a so-called TFT-type (thinfilm transistor type) radiographic image detector. Alternatively, the radiographic image detector may be a so-called optical-readout-type radiographic image detector.

Further, the yawing table may be generated in any manner as long as the yawing table stores the inclination angle of the radiographic image detector for each position of the radiographic image detector. For example, the yawing table may be generated by obtaining an image for calibration by performing radiography with a vertically-extending jig placed on the radiographic image detector, by detecting the inclination angle of an image of the jig in the image for calibration, and by correlating the detected inclination angle with position information about the radiographic image detector. Alternatively, the yawing table may be generated by moving the radiographic image detector with an inclination sensor attached to the radiographic image detector.

Further, the yawing table may store the center of rotation of the inclination angle together with the inclination angle at each position.

Further, the image correction means may have a function of correcting the inclination of the radiographic image based on an input from an input means, and the inclination angle stored in the yawing table may be replaced with an inclination angle when the inclination of the radiographic image is corrected based on the input from the input means.

The radiographic image detection apparatus of the present invention is a radiographic image detector apparatus comprising:

a radiation source that outputs radiation to a subject;

a radiographic image detector that detects, as a radiographic image, the radiation that has been output from the radiation source and transmitted through the subject;

a detector movement means that moves the radiographic image detector parallel to a radiation detection surface of the radiographic image detector;

a yawing table that stores an inclination angle of the radiographic image detector at each position of the radiographic image detector within a movement range of the radiographic image detector by the detector movement means;

an image correction means that corrects, based on the position of the radiographic image detector when each of a plurality of radiographic images is obtained by the radiographic image detector moved to different positions from each other, inclination of the plurality of radiographic images respectively by using the yawing table; and an image synthesis means that produces a synthesis image by combining the plurality of radiographic images corrected by the image correction means. Therefore, according to the radiographic image detection apparatus of the present invention, when the radiographic image detector is moved by the detector movement means, it is possible to correct the inclination of the radiographic image at high speed by using a yawing table that has stored the inclination angle of the radiographic image detector at each position in advance. The inclination of the radiographic image is corrected by utilizing the characteristic that the inclination of the radiographic image detector at each position recurs (recurrence characteristic).

Further, when the yawing table is generated by obtaining an image for calibration by performing radiography with a vertically-extending jig placed on the radiographic image detector, by detecting the inclination angle of an image of the jig in the image for calibration, and by correlating the detected inclination angle with position information about the radiographic image detector, the inclination angle is detected based on the image for calibration that has been obtained through the actual radiography procedure. Therefore, it is possible to accurately correct the inclination of the radiographic image.

Further, when the image correction means has a function of correcting the inclination of the radiographic image based on an input from an input means, and the inclination angle stored in the yawing table is replaced with an inclination angle when the inclination of the radiographic image is corrected based on the input from the input means, even if the inclination angle of the radiographic image detector at each position stored in the yawing table becomes different from an actual inclination angle by a change in the detector movement means due to passage of time or the like, it is possible to replace the stored inclination angle with a correct inclination angle, in which the difference is corrected. Therefore, it is possible to accurately correct the inclination of the radiographic image.

Further, when the yawing table stores the center of rotation of the inclination angle of the radiographic image detector together with the inclination angle of the radiographic image detector at each of the positions, even if the center of rotation of the inclination angle of the radiographic image detector is shifted from the center of the radiographic image, it is possible to accurately correct the inclination of the radiographic image.

DESCRIPTION OF THE PREFERRED EMBODIMENTS

Figure 1:
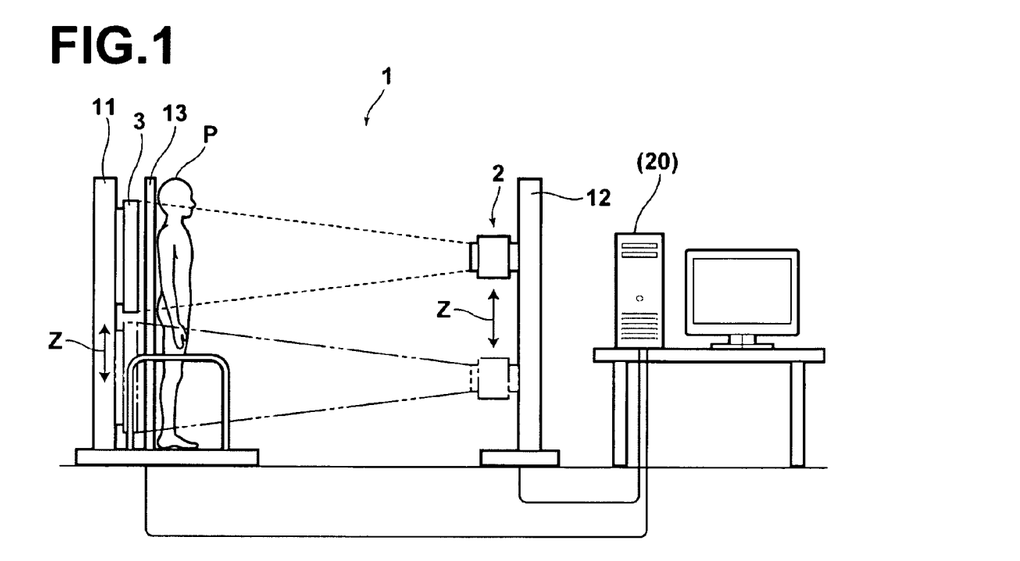
FIG. 1 is a schematic diagram illustrating an embodiment of a radiographic image detection apparatus of the present invention.
Figure 2:
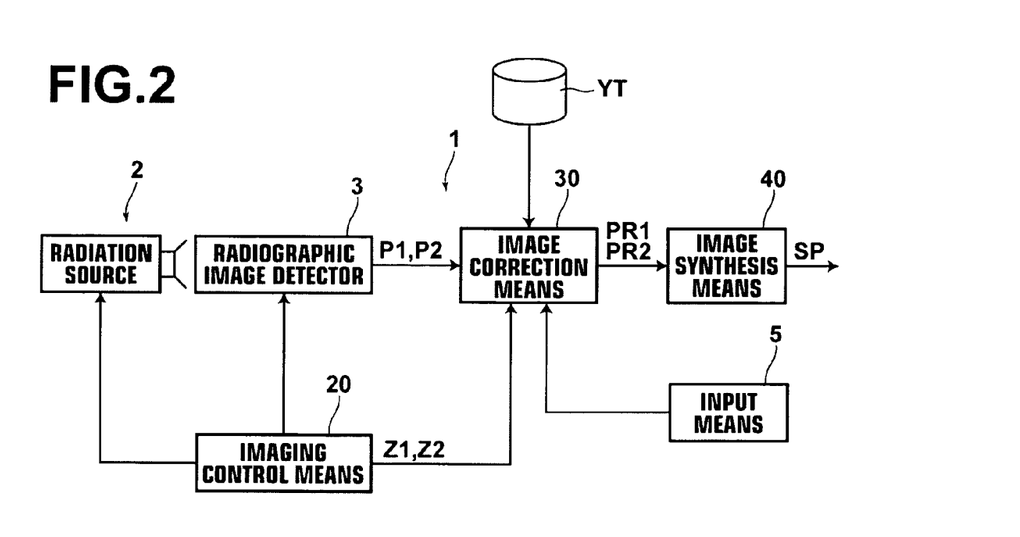
FIG. 2 is a block diagram illustrating an embodiment of a radiographic image detection apparatus of the present invention.

Hereinafter, embodiments of the present invention will be described in detail with reference to drawings. FIG. 1 is a schematic diagram illustrating a side view of a radiographic image detection apparatus according to an embodiment of the present invention. FIG. 2 is a block diagram illustrating an embodiment of the radiographic image detection apparatus of the present invention. A radiographic image detection apparatus 1 illustrated in FIGS. 1 and 2 can perform two kinds of radiography, namely, so-called long-size radiography (longitudinal radiography) and ordinary radiography. In the long-size radiography, radiography is performed a plurality of times to obtain radiographic images of different regions of a subject. In the ordinary radiography, radiography is performed on a predetermined region of the subject. When the long-size radiography is performed, a screen 13 is attached to the radiographic image detection apparatus 1, and when the ordinary radiography is performed, the screen 13 is removed from the radiographic image detection apparatus 1.

The radiographic image detection apparatus 1 includes a radiation source 2, a radiographic image detector 3, an imaging control means 20, an image correction means 30 and an image synthesis means 40. The radiation source 2 irradiates subject S with radiation. The radiation source 2 is controlled by the imaging control means 20. The radiographic image detector 3 illustrated in FIG. 1 stores, as a static latent image, radiographic image information represented by radiation that has passed through the subject S. Further, the static latent image stored in the radiographic image detector 3 is read out to detect the distribution of transmittance of radiation as the radiographic image. The configuration and structure of the radiographic image detector 3 is not limited as long as the radiographic image detector 3 can detect radiation and output the detected radiation as image information. For example, the radiographic image detector 3 may be a solid-state detector of TFT type, a solid-state detector of optical readout type and the like.

A detector movement means 11 moves the radiographic image detector 3 in a vertical direction (in the direction of arrow Z) along the detection surface. For example, the detector movement means 11 includes a rail and a drive means, such as a bearing and a motor. Meanwhile, a radiation source movement means 12 moves the radiation source 2 in the vertical direction (in the direction of arrow Z) so that the irradiation position of radiation is changed to correspond to the position of the radiographic image detector 3. In FIG. 1, the radiation source 2 is moved synchronously with the radiographic image detector 3 to change the irradiation position.

Alternatively, the irradiation position of radiation may be changed by swinging the radiation source 2.

The imaging control means 20 controls the imaging operation (radiography operation) by the radiographic image detection apparatus 1. The imaging control means 20 automatically correlates the positions of regions of the subject S with the positions of the radiation source 2 and the radiographic image detector 3 based on information about the imaging range with respect to the subject S and information about an actual imaging range. Further, the imaging control means 20 controls each apparatus (device and unit) so that the subject is imaged at an optimum dose of radiation in each imaging (radiography). The imaging control means 20 controls imaging, for example, in such a manner that first imaging (radiography) is performed on the vicinity of the head of the subject S and the second imaging (radiography) is performed on the vicinity of the chest of the subject S. Further, the imaging control means 20 determines the radiation dose based on the control operation.

Figure 3:
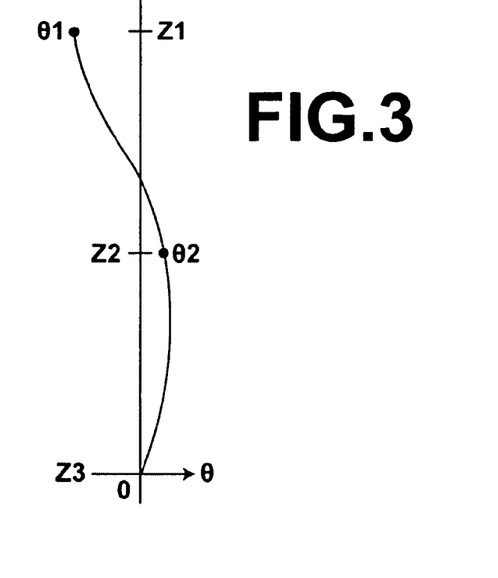
FIG. 3 is a graph showing an example of a yawing table illustrated in FIG. 2.

The image correction means 30 corrects the inclination of the radiographic image based on the position of the radiographic image detector 3 at the time of obtainment of the radiographic image. The image correction means 30 corrects the inclination of the radiographic image by referring to yawing table YT. The yawing table YT stores inclination angle $\theta$ corresponding to the position of the radiographic image detector 3, for example, as illustrated in FIG. 3.

Figure 4:
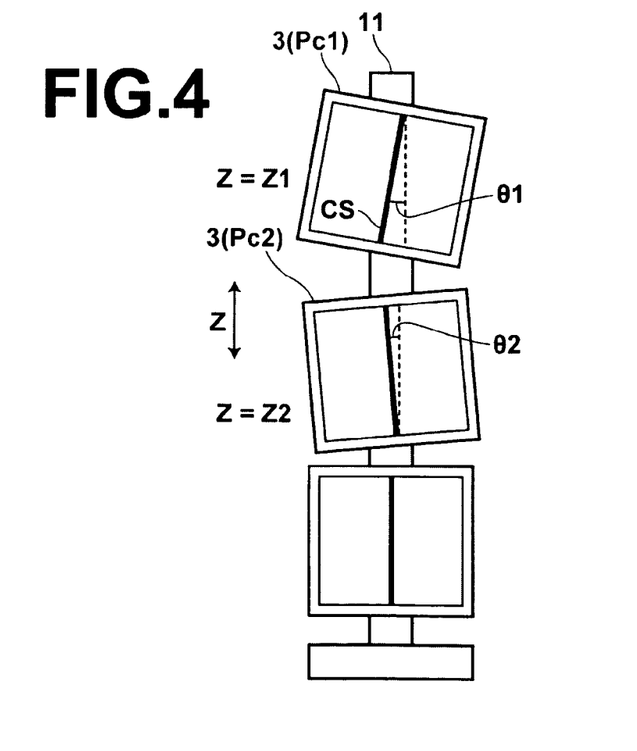
FIG. 4 is a schematic diagram illustrating the way of generating the yawing table illustrated in FIG. 3.

The yawing table YT is generated in the following manner. First, a vertical jig is arranged on the detection surface side of the radiographic image detector 3. As illustrated in FIG. 4, the jig is imaged while the position of the radiographic image detector 3 is changed to obtain a plurality of images Pc1, Pc2 for calibration. Then, the inclination of the image of the jig in each of the images Pc1, Pc2 is detected as inclination angles $\theta 1$, $\theta 2$ at positions Z1, Z2 of the radiation image detector 3. Accordingly, the yawing table YT, as illustrated in FIG. 3, in which each position Z and the inclination angle $\theta$ are correlated with each other is generated. As described above, the images Pc1, Pc2 for calibration are obtained through the same procedure as actual radiography, and the inclination angles $\theta$ are detected based on the images Pc1, Pc2 for calibration. Therefore, it is possible to more accurately correct the inclination of the radiographic image.

Figure 5A:
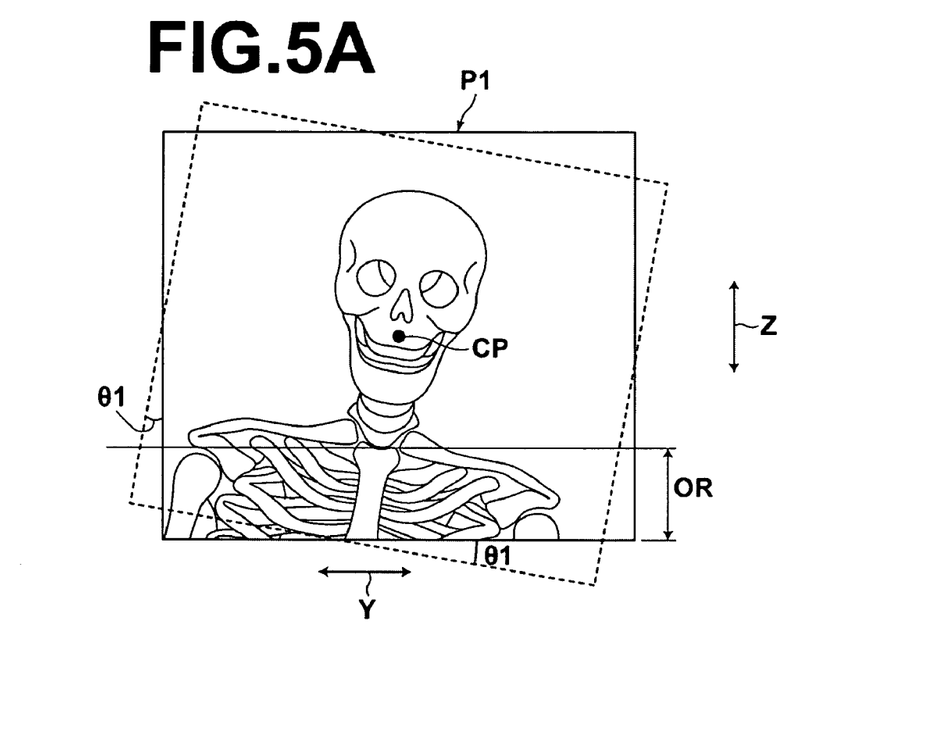
FIG. 5A is a schematic diagram illustrating an example of a radiographic image detected when a radiographic image detector illustrated in FIG. 2 is inclined.
Figure 5B:
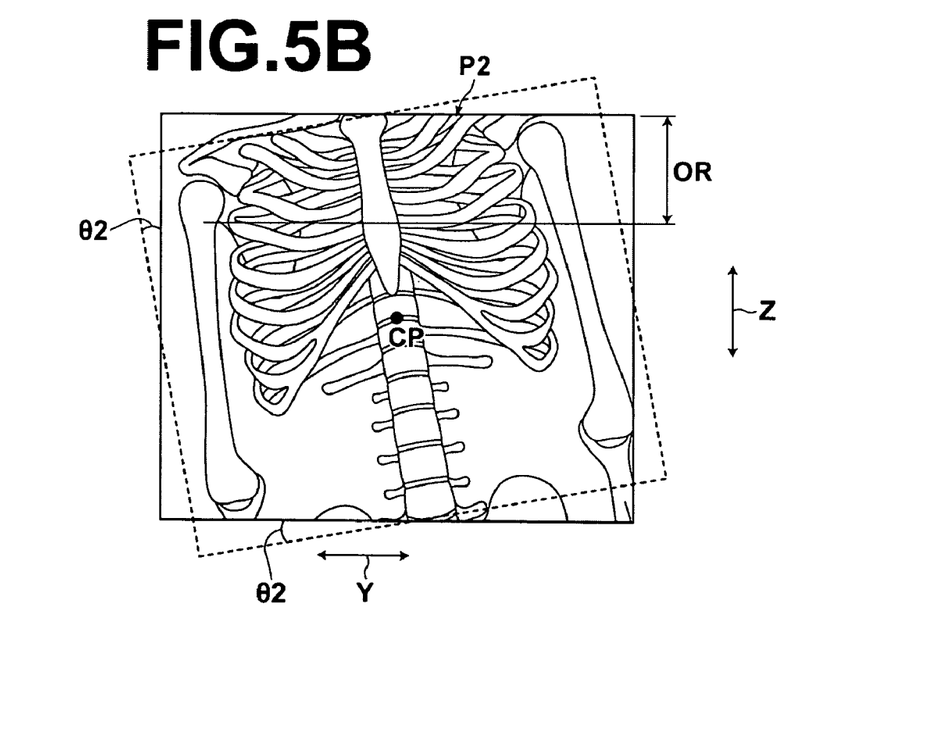
FIG. 5B is a schematic diagram illustrating an example of a radiographic image detected when the radiographic image detector illustrated in FIG. 2 is not inclined.

The image correction means 30 illustrated in FIG. 2 obtains position information at the time of detection of each of the radiographic images from the imaging control means 20. Further, the image correction means 30 extracts inclination angle $\theta$ that is correlated with the obtained position information from the yawing table YT. Then, the image correction means 30 corrects the inclination of each of the radiographic images by using the inclination angle $\theta$ extracted from the yawing table YT. For example, when the radiographic image detector 3 is positioned at positions Z1, Z2 and a plurality of radiographic images P1, P2, as illustrated in FIGS. 5A and 5B, are obtained, the image correction means 30 extracts inclination angle $\theta 1$ at position Z1 from the yawing table YT (please refer to FIG. 3), and corrects the inclination of the radiographic image P1. Similarly, the image correction means 30 extracts inclination angle $\theta 2$ at position Z2 from the yawing table YT (please refer to FIG. 3), and corrects the inclination of the radiographic image P2.

Here, for the purpose of explanation, a case in which the center of rotation is located at a central part (center) of the radiographic image has been used as an example in FIGS. 3, 4, 5A and 5B. The inclination angle $\theta$ of the radiation source 2 or the radiographic image detector 3 is caused by the structure of the detector movement means 11 (the relationship between the rail and the bearing). Therefore, the center CP of rotation of inclination is not always at the center of the radiographic image detector 3. Therefore, in addition to the inclination angle $\theta$, the center CP of rotation may be stored in the yawing table YT in such a manner to be correlated with each position. At this time, the image correction means 30 rotates the radiographic image P1 by inclination angle—$\theta$ with respect to the center CP of rotation stored in the yawing table YT.

Further, the image correction means 30 may have a function of correcting the inclination of the radiographic image based on an input from an input means 5. Specifically, rotation correction processing may be performed by an operator based on a radiographic image displayed on a display unit. The rotation correction processing may be performed by the operator by using the input means 5, such as a mouse or a keyboard. At this time, the image correction means 30 detects the inclination angle $\theta$ when the rotation correction is performed by the input means 5, and updates the inclination angle stored in the yawing table YT by replacing the stored inclination angle with the detected inclination angle $\theta$. Accordingly, even if the recurrence characteristics of the inclination angle $\theta$ stored in the yawing table YT are shifted by a change in the detector movement means 11 due to passage of time or the like, it is possible to accurately correct rotation in such a manner that manual rotation correction is not necessary when the next radiography is performed.

Figure 6:
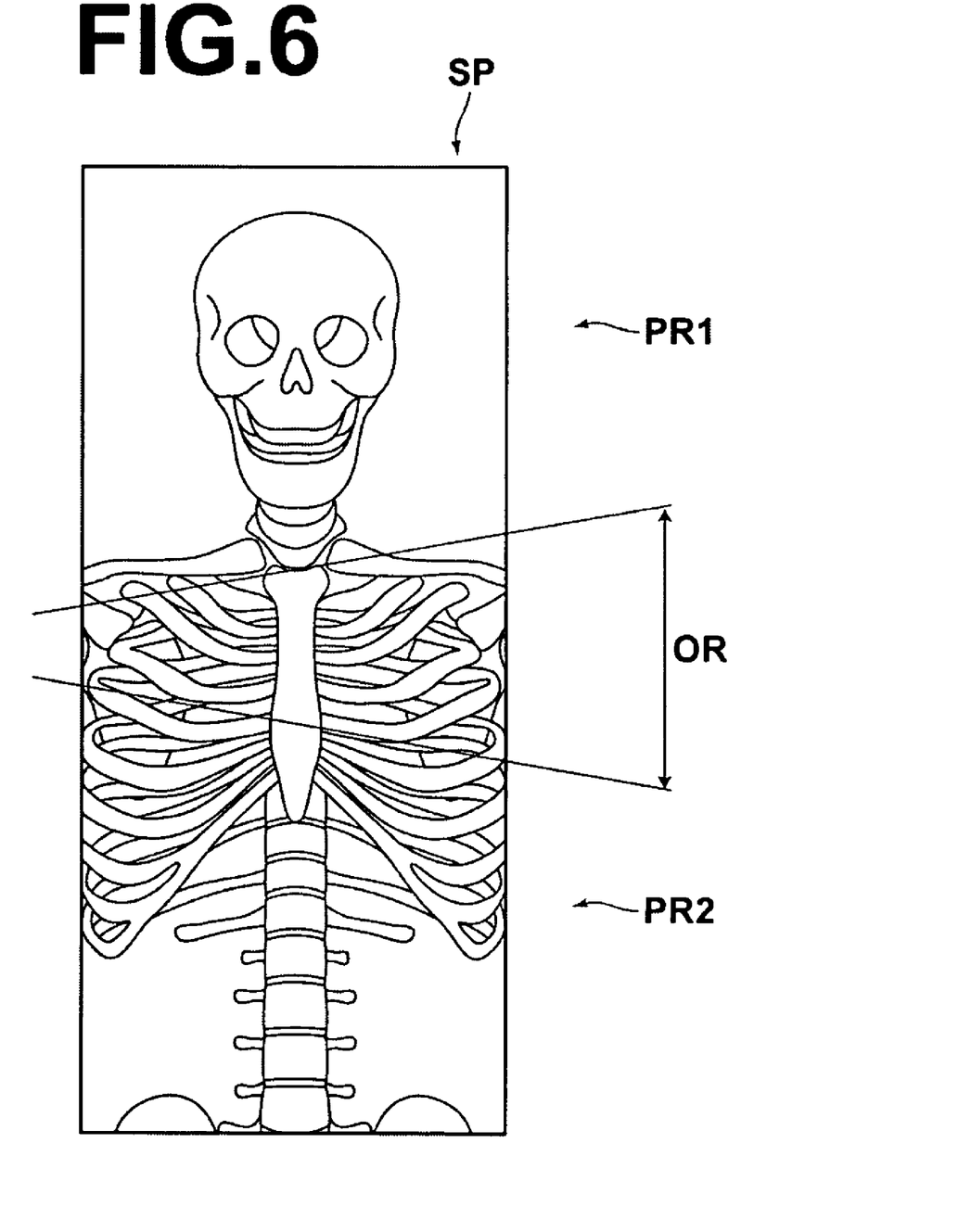
FIG. 6 is a schematic diagram illustrating an example of a synthesis image produced by an image synthesis means illustrated in FIG. 2.

The image synthesis means 40 illustrated in FIG. 2 generates synthesis image SP as illustrated in FIG. 6 by combining a plurality of radiographic images P1, P2 obtained in long-size radiography. Here, position matching is performed on the plurality of radiographic images P1, P2 by performing pattern matching line by line. When the correlation becomes the highest, image synthesis is performed. Further, the image synthesis means 40 synthesizes an overlap portion OR of images that are adjacent to each other by addition average processing. The synthesis processing is not limited to the addition average processing. Alternatively, known image processing, such as weighted addition processing, may be performed.

The image synthesis means 40 may have a function of adjusting the density characteristics of each of the radiographic images P1, P2 before synthesis. The density may be adjusted by using a known technique. For example, histograms are generated for the radiographic images P1 and P2, and automatic adjustment is performed, based on the histograms, so that the densities and contrasts of the images approximate to each other. At this time, the density or contrast of each image may be adjusted based on the density or contrast of a predetermined base image (for example, first image, which was obtained first in a series of images). Alternatively, a value may be set as a base density or a base contrast in advance, and the density or contrast of each of the images may be adjusted based on the base density or the base contrast.

As described above, the yawing table YT is prepared in advance, and the inclination is corrected based on the position of the radiographic image detector 3 at the time of obtainment of the radiographic image. Therefore, it is possible to correct the inclination at high speed. Specifically, in a conventional method in which the inclination is corrected based on a marker, it is necessary to perform pattern matching, which is time consuming. Therefore, in the conventional method, it is impossible to perform high-speed correction. Meanwhile, the inclination of the radiographic image detector 3 is caused by a mechanical structure, such as the relationship between the rail and the bearing as described above. Therefore, there is a characteristic that the inclination angle $\theta$ at each position of the radiographic image detector 3 recurs at high possibility (high recurrence characteristic). If a yawing table YT is prepared in advance by utilizing this characteristic of the inclination angle, and the inclination is corrected based on inclination angle θ extracted from the yawing table YT by searching the yawing table YT, it is possible to correct inclination at high speed.

Figure 7:
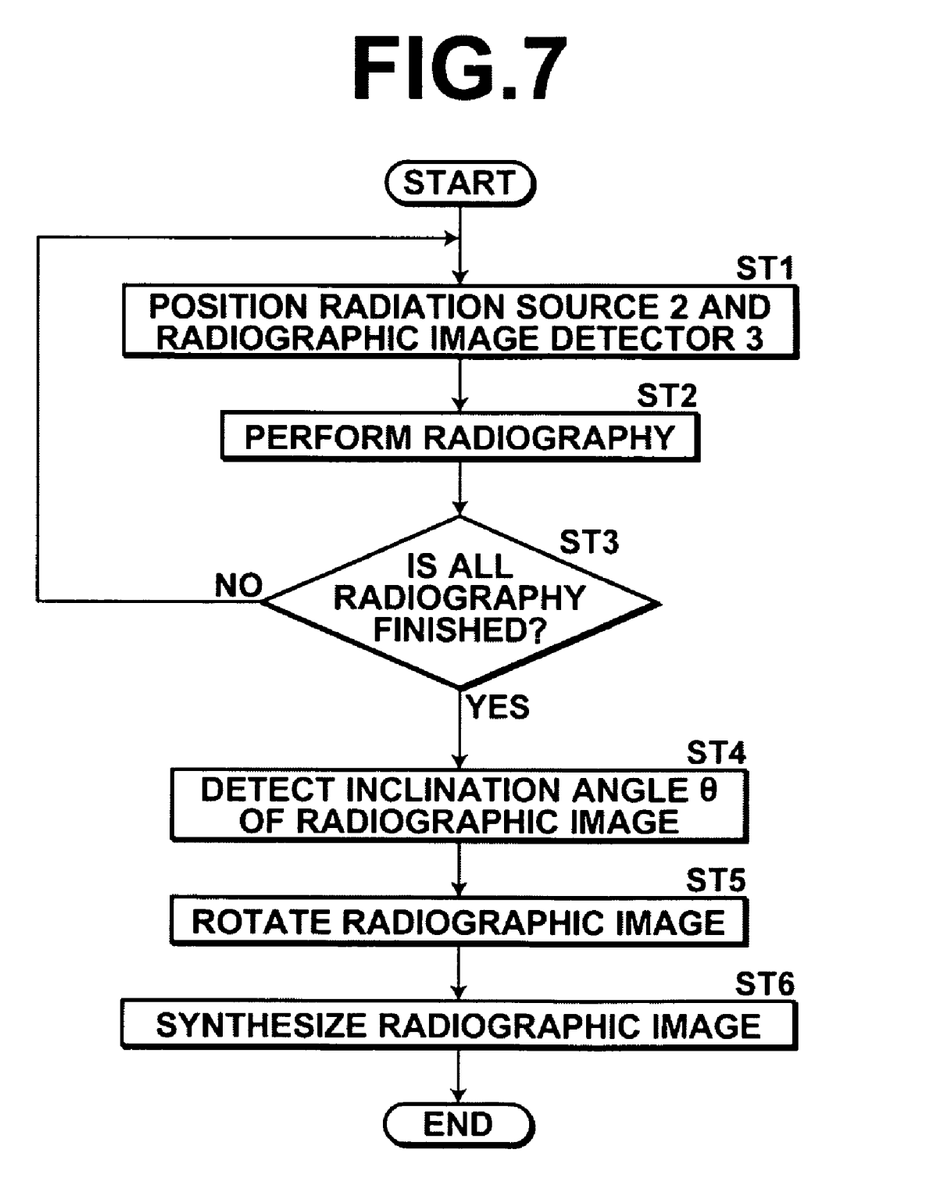
FIG. 7 is a flow chart showing an example of operations by the radiographic image detection apparatus of the present invention.

FIG. 7 is a flowchart showing an example of operations of a radiographic image detection apparatus of the present invention. The example of the operations will be described with reference to FIGS. 1 through 7. First, subject S stands in front of the screen 13, and the radiation source 2 and the radiographic image detector 3 are positioned (step ST1). Then, the subject S is irradiated with radiation output from the radiation source 2, and radiation that has passed through the subject S is detected, as a radiographic image, by the radiographic image detector 3 (step ST2). A predetermined number of times of radiography is performed while the positions of the radiation source 2 and the radiographic image detector 3 are changed to detect a plurality of radiographic images P1, P2 (step ST1 through step ST3).

Next, the image correction means 30 refers to the yawing table YT, and extracts inclination angle θ1, based on the position information Z1 about the radiographic image detector 3 at the time of obtainment of the radiographic image P1, from the yawing table YT. Similarly, the image correction means 30 refers to the yawing table YT, and extracts inclination angle θ2, based on the position information Z2 about the radiographic image detector 3 at the time of obtainment of the radiographic image P2, from the yawing table YT (step ST4, please refer to FIG. 4). Further, the image correction means 30 corrects the inclination of each of the radiographic images P1, P2 by using the extracted inclination angles θ1, θ2, respectively (step ST5, please refer to FIGS. 5A and 5B). After then, the image synthesis means 40 combines a plurality of radiographic images PR1, PR2 the inclination of which has been corrected, and produces a long-size synthesis image SP (step ST6, please refer to FIG. 6).

According to the aforementioned embodiments, the radiographic image detection apparatus of the present invention includes the radiation source 2 that outputs radiation to a subject, the radiographic image detector 3, the detector movement means 11, the yawing table YT, the image correction means 30, and the image synthesis means 40. The radiographic image detector 3 detects, as a radiographic image, the radiation that has been output from the radiation source 2 and transmitted through the subject, and the detector movement means 11 moves the radiographic image detector 3 parallel to a radiation detection surface of the radiographic image detector 3 (along the radiation detection surface). Further, the yawing table YT stores inclination angle θ of the radiographic image detector 3 at each position Z of the radiographic image detector 3 within a movement range of the radiographic image detector 3 by the detector movement means 11. The image correction means 30 corrects, based on the position of the radiographic image detector 3 when each of a plurality of radiographic images P1, P2 is obtained by the radiographic image detector 3 moved to different positions from each other, inclination of the plurality of radiographic images P1, P2 respectively by using the yawing table YT. The image synthesis means 40 produces synthesis image SP by combining the plurality of radiographic images that have been corrected by the image correction means 30. Therefore, when the radiographic image detector 3 is moved by the detector movement means 11, the features that the inclination of the radiographic image detector 3 at each position tends to recur (recurrence characteristic) are utilized, and the inclination of each of the radiographic images is corrected at high speed by using the yawing table YT, which stores the inclination angle θ at each position Z in advance.

Further, as illustrated in FIG. 4, when the yawing table YT is generated by obtaining image Pc for calibration by performing radiography with a vertically-extending jig placed on the radiographic image detector 3, by detecting the inclination angle of an image of the jig in the image Pc for calibration, and by correlating the detected inclination angle with position Z of the radiographic image detector 3, the inclination angle θ is detected based on the image Pc for calibration that has been obtained through an actual radiography procedure. Therefore, it is possible to accurately correct the inclination of the radiographic image.

As illustrated in FIG. 2, when the image correction means 30 has a function of correcting the inclination of the radiographic image based on an input from the input means 5, and the inclination angle stored in the yawing table YT is replaced with an inclination angle when the inclination of the radiographic image is corrected based on the input from the input means 5, even if the inclination angle θ of the radiographic image detector 3 at each position Z, which is stored in the yawing table YT, is shifted from an actual inclination angle by a change in the detector movement means 11 due to passage of time or the like, the stored inclination angle θ can be replaced with a correct inclination angle θ, in which the shift in the inclination angle has been corrected. Therefore, it is possible to accurately correct the inclination of the radiographic image.

The embodiments of the present invention are not limited to the aforementioned embodiments. For example, a case in which the yawing table YT is generated based on an image for calibration has been described. However, it is not necessary to generate the yawing table YT in such a manner. For example, an inclination sensor may be attached to the radiographic image detector 3, and the inclination angle θ may be detected by the inclination sensor.

What is claimed is:

1. A radiographic image detection apparatus comprising:
a radiation source that outputs radiation to a subject;
a radiographic image detector that detects, as a radiographic image, the radiation that has been output from the radiation source and transmitted through the subject;
a detector movement means that moves the radiographic image detector parallel to a radiation detection surface of the radiographic image detector;
a yawing table that stores an inclination angle of the radiographic image detector at each position within a movement range of the radiographic image detector by the detector movement means;
an image correction means that corrects, based on the position of the radiographic image detector when each of a plurality of radiographic images is obtained by the radiographic image detector moved to different positions from each other, inclination of the plurality of radiographic images respectively by using the yawing table; and
an image synthesis means that produces a synthesis image by combining the plurality of radiographic images corrected by the image correction means.

2. A radiographic image detection apparatus, as defined in claim 1, wherein the yawing table is generated by obtaining an image for calibration by performing radiography with a vertically-extending jig placed on the radiographic image detector, by detecting the inclination angle of an image of the jig in the image for calibration, and by correlating the detected inclination angle with position information about the radiographic image detector.

3. A radiographic image detection apparatus, as defined in claim 1, wherein the image correction means has a function of correcting the inclination of the radiographic image based on an input from an input means, and wherein the inclination angle stored in the yawing table is replaced with an inclination angle when the inclination of the radiographic image is corrected based on the input from the input means.

4. A radiographic image detection apparatus, as defined in claim 1, wherein the yawing table stores the center of rotation of the inclination angle of the radiographic image detector together with the inclination angle of the radiographic image detector at each of the positions.

* * * * *